United States Patent [19]

Veber et al.

[11] 4,108,987
[45] Aug. 22, 1978

[54] CYCLIC HEXAPEPTIDES

[75] Inventors: Daniel F. Veber, Ambler; Stephen F. Brady, Philadelphia; Sandor L. Varga, Harleysville, all of Pa.

[73] Assignee: Merck & Co., Inc., Rahway, N.J.

[21] Appl. No.: 832,501

[22] Filed: Sep. 12, 1977

Related U.S. Application Data

[63] Continuation-in-part of Ser. No. 710,491, Aug. 2, 1976, abandoned.

[51] Int. Cl.[2] .................. A61K 37/00; C07C 103/52
[52] U.S. Cl. ..................... 424/177; 260/112.5 R; 426/634; 426/658
[58] Field of Search .............. 260/112.5 R; 424/177; 426/658, 634

[56] References Cited

PUBLICATIONS

K. Kopple, et al., J. Am. Chem. Soc. 96, 2597–2605, (1974).
C. Deber, et al., Israel Journ. of Chem. 12, (1–2), 15–29, (1974).
V. Ivanov, et al., Chem. of Natural Compounds Khim Prirod, Soedin., 57(1), 63–66, (1975).

*Primary Examiner*—Delbert R. Phillips
*Attorney, Agent, or Firm*—Walter Patton

[57] ABSTRACT

Synthetic novel cyclic hexapeptides having the structure:

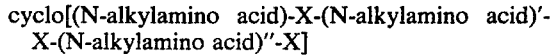

wherein (N-alkylamino acid), (N-alkylamino acid)' and (N-alkylamino acid)" have the structure:

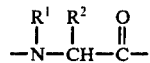

wherein $R^1$ is a lower alkyl group having 1 to 3 carbon atoms and $R^2$ is hydrogen and methyl or $R^1$ and $R^2$ are $(CH_2)_n$, $n$ being an integer 2 or 3, and form a 4- or 5-membered ring; and X is D- or L-Ala, D- or L-Phe, D- or L-Leu, D- or L-p-halophenylalanyl or D- or L-p-nitrophenylalanyl, with the proviso that when $R^1$ is methyl and $R^2$ is hydrogen, X is not D-Ala are prepared. Oral administration of these cyclic peptides improves the digestive efficiency of certain herbivorous animals.

11 Claims, No Drawings

CYCLIC HEXAPEPTIDES

This application is a continuation-in-part application of co-pending application U.S. Ser. No. 710,491, filed Aug. 2, 1976, now abandoned.

BACKGROUND OF THE INVENTION

For many years, the animal science industry has tried to increase the efficiency of feed utilization in both ruminant and non-ruminant animals. More study has been done in ruminant animals because of their greater economic importance.

In the source of investigating the efficiency of feed use, the mechanism by which ruminants digest and degrade the components of their feed to form molecules which can be metabolically utilized has been intensively studied. Aspects of the mechanism of carbohydrate utilization are now known. Microorganisms in the rumen of the animal ferment carbohydrates to produce monosaccharides, and then degrade the monosaccharides to pyruvate.

Pyruvate is then metabolized by microbiological processes to either acetate or propionate, which may be either acids or derivatives of the acids. Two acetates may be combined thereafter, still in the rumen, to form butyrate. Leng, "Formation and Production of Volatile Fatty Acids in the Rumen." Physiology of Digestion and Metabolism in the Ruminant (Phillipson et al., ed.), Oriel Press, pp. 408–410.

The animal can utilize butyrate, propionate, and acetate with differing degrees of efficiency. (Smith, Gary E. 1971. Energy Metabolism and Metabolism of Volatile Fatty Acids. Digestive Physiology and Nutrition of Ruminants. O.S.U. Book Stores. Corvallis, Oregon). Utilization of these compounds, which are collectively known as volatile fatty acids (VFA), occurs after absorption from the gut of the animal. Butyrate is utilized most efficiently, and acetate the least efficiently. However, the relative efficiency of use of butyrate is negated by the inefficiency of the manufacture of butyrate, which must be made from acetate in the rumen.

The process of formation of acetate in the rumen is one of the major inefficiencies in the rumen. Since acetate is made by the degradation of a pyruvate molecule, each molecule of acetate which is produced is accompanied by a one carbon molecule which subsequently results in the formation of methane. Most of the methane produced is lost through eructation. Since butyrate is made from two molecules of acetate, each molecule of the relatively efficiently used butyrate involves the loss to the animal of two molecules of methane, with all of the associated energy.

Thus, the efficiency of carbohydrate utilization (carbohydrates, being the major nutritive portion of ruminant animals' feed) can be increased by treatments which encourage the animal to produce propionate and butyrate rather than acetate from carbohydrates. Further, the efficiency of feed use can be effectively monitored by observing the production and concentration of propionate compounds in the rumen. If the animal is making more propionates, it will be found to be using its feed more efficiently.

The efficiency of feed utilization by a ruminant animal can readily be determined by chemical analysis for acetate and propionate produced by the fermentation occurring in the rumen or more conveniently by chemical analysis of the rumen contents for acetate and propionate using an in vitro rumen fermentation test.

DESCRIPTION OF THE INVENTION

It is the object of the present invention to provide novel cyclic hexapeptides having the structure:

cyclo[(N-alkylamino acid)-X-(N-alkylamino acid)'-X-(N-alkylamino acid)"-X]

wherein (N-alkylamino acid), (N-alkylamino acid)' and (N-alkylamino acid)" have the structure:

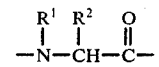

wherein $R^1$ is a lower alkyl group having 1 to 3 carbon atoms and $R^2$ is hydrogen and methyl or $R^1$ and $R^2$ are $-(CH_2)_n-$, $n$ being an integer 2 or 3, and form a 4- or 5-membered ring; and X is D- or L-Ala, D- or L-Phe, D- or L-Leu, D- or L-p-halophenylalanyl or D- or L-p-nitrophenylalanyl, with the proviso that when $R^1$ is methyl and $R^2$ is hydrogen, X is not D-Ala wherein halo is selected from the group consisting of fluorine, chlorine, bromine and iodine which are useful for improving ruminant feed utilization.

Further preferred cyclic hexapeptides of the present invention are those wherein (N-alkylamino acid), (N-alkylamino acid)' and (N-alkylamino acid)" are selected from the group consisting of Sar, D- or L-Pro and X is D- or L-Ala or D- or L-Phe and wherein when Pro is D, X is L-Ala, L-Phe, L-p-chlorophenylalanyl or L-p-nitrophenylalanyl; and when Pro is L, X is D-Ala, D-Phe, D-p-chlorophenylalanyl or D-p-nitrophenylalanyl; and wherein when N-alkylamino acid is Sar, X is not D-Ala or D- or L-Phe.

Still further preferred cyclic hexapeptides of the present invention are those having the structure:

cyclo(D-Pro-Ala)$_3$, cyclo(D-Pro-Phe)$_3$, cyclo(Pro-D-Phe)$_3$, cyclo(Sar-Ala)$_3$, cyclo(Pro-D-Ala)$_3$, cyclo(Sar-D-Phe)(Pro-D-Phe)$_2$, and cyclo(p-chlorophenylalanyl-D-Pro)$_3$ of which the peptides having the structure:

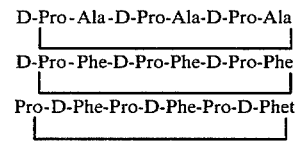

are the most preferred for improving ruminant feed utilization.

It is a further object of the present invention to provide for feed compositions useful in improving feed utilization. A further aspect of the present invention is a method of improving feed utilization by ruminants having a developed rumen function which comprises oral administration to the ruminants of an effective VFA-increasing amount of the above mentioned novel cyclic hexapeptides. A still further aspect of the present invention is the process for the synthetic preparation of the novel cyclic hexapeptides of the present invention.

The cyclic hexapeptides of the present invention are useful to ruminants which have a developed rumen function. Young ruminants, basically those still unweaned, function as monogastric animals. They use their simple liquid feeds just as monogastric animals do. As the young ruminants begin to eat solid feed containing cellulose, starch, and other carbohydrates, the function of the rumen begins to develop, and the microbiological population of the rumen increases. After the animal has eaten solid feed for a time, its rumen reaches its full development and continues to operate throughout the animal's life.

The present invention is functional in all of the ruminants, that is, the animals which have multiple stomachs, one of which is a rumen. The economically-important ruminant animals are cattle, sheep and goats.

In accordance with the present invention, the novel cyclic hexapeptides are prepared by cyclizing the corresponding linear hexapeptides. The linear hexapeptides are prepared by using the solid phase sequential synthesis technique. Accordingly, the process for preparing the cyclic hexapeptides of the present invention comprises (a) preparing the corresponding blocked linear hexapeptide attached to a solid phase resin; (b) removing the blocked linear hexapeptide from the resin and deblocking; and (c) treating the deblocked linear hexapeptide with a cyclizing agent to obtain the cyclic hexapeptide.

When the linear hexapeptide is prepared on the resin, it is not critical which amino acid is selected to be at the C-terminal position provided only that the sequence of amino acids in the linear hexapeptide is the same as that in the desired cyclic hexapeptide. Once a linear hexapeptide has been cyclized one can no longer determine which amino acid was at the C-terminus of the linear hexapeptide. As an example to illustrate this, either of the two following linear hexapeptides, when cyclized, will give the identical cyclic hexapeptide:

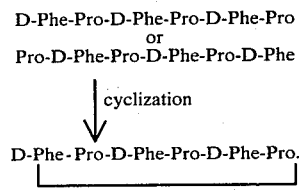

Herein below, in the further description of the synthesis of the peptides, the reagents used will be first listed by their chemical name and their common abbreviation in parenthesis. Thereafter, the reagent will be referred to by the common abbreviation.

For convenience, a table of relevant abbreviations is provided:

| Abbreviated Designation | amino acid |
|---|---|
| Pro | L-proline |
| Sar | sarcosine |
| Ala | L-alanine |
| D-Ala | D-alanine |
| N-MeAla | L-N-methyl alanine |
| D-N-MeAla | D-N-methyl alanine |
| Phe | L-phenylalanine |
| D-Phe | D-phenylalanine |
| Leu | L-leucine |
| D-Leu | D-leucine |
| Abbreviated Designation | Protecting Groups |
| BOC | tert-butyloxycarbonyl |
| OMe | methyl ester |
| tBu | tert-butyl |
| CBZ | benzyloxycarbonyl |
| Abbreviated Designation | Activating Groups |
| NPE | p-nitrophenyl ester |
| HSE or NHS | N-hydroxysuccinimide ester |
| HBT | 1-hydroxybenzotriazole |
| Abbreviated Designation | Condensing Agents |
| DCCI | dicyclohexylcarbodiimide |

| Abbreviated Designation | Reagents |
|---|---|
| TFA | trifluoroacetic acid |
| TEA | triethylamine |
| Abbreviated Designation | Solvents |
| CMW | chloroform-methanol-water |
| DMF | dimethylformamide |
| THF | tetrahydrofuran |

The synthesis of the linear hexapeptides by the solid phase technique is conducted in a stepwise manner on chloromethylated resin. The resin is composed of fine beads (20–70 microns in diameter) of a synthetic resin prepared by copolymerization of styrene with 1 to 2 percent divinylbenzene. The benzene rings in the resin are chloromethylated in a Friedel-Crafts reaction with chloromethyl methyl ether and stannic chloride. The chlorine in benzyl chloride is attached by a reactive type of linkage. The Friedel-Crafts reaction is continued until the resin contains 0.5 to 5 mmoles of chlorine per gram of resin.

The amino acid selected to be the C-terminal amino acid of the linear hexapeptide is converted to its amino protected derivative. The carboxyl group of the selected C-terminal amino acid is bound covalently to an insoluble polymeric resin support, as for example, as the carboxylic ester of the resin-bonded benzyl chloride present in chloromethyl-substituted polystyrene-divinylbenzene resin. After the amino protecting group is removed, the amino protected derivative of the next amino acid in the sequence is added along with a coupling agent, such as dicyclohexylcarbodiimide. The amino acid reactant may be employed in the form of a carboxyl-activated amino acid such as the NHS ester, an amino acid azide, and the like. Deprotection and addition of successive amino acids is performed until the desired linear hexapeptide is formed.

Amino-protecting groups ordinarily employed include those which are well known in the art, for example, urethane protecting substituents such as benzyloxycarbonyl (carbobenzoxy), p-methoxycarbobenzoxy, p-nitrocarbobenzoxy, t-butyloxycarbonyl, and the like. It is preferred to utilize t-butyloxycarbonyl (BOC) for protecting the α-amino group in the amino acids undergoing reaction at the carboxyl end of said amino acid. The BOC protecting group is readily removed following such coupling reaction and prior to the subsequent step by the action of relatively mild acids (i.e., trifluoroacetic acid, or hydrogen chloride in ethyl acetate).

The selection of protecting groups is, in part, dictated by particular coupling conditions, in part by the amino acid and peptide components involved in the reaction.

After the linear hexapeptide has been formed on the solid phase resin, it may be removed by a variety of methods which are well known in the art. For example, the peptide may be cleaved from the resin with hydrazine and thus directly form the peptide hydrazine which may be subsequently cyclized via the azide to the desired cyclic hexapeptide. Alternatively, the peptide may be removed from the resin by treatment with a lower alcohol such as methanol in the presence of an organic base such as triethylamine, thus resulting in the formation of the corresponding lower alcohol ester of the linear hexapeptide. In the case wherein the ester is the methyl ester, the resulting compound may be converted to the azide via the hydrazide which may then be cyclized to the desired cyclic hexapeptide by methods known in the prior art. Alternatively, the methyl ester can be saponified under mild conditions such as at pH 11 to 12; the BOC group can be removed by the action of the relatively mild acid, hydrogen chloride in ether acetate and the resulting linear deblocked hexapeptide can be cyclized to the desired cyclic hexapeptide by methods known in the art such as treatment with diphenylphosphoryl azide. The preferred methods of removing the blocked linear hexapeptide from the resin is by treatment with anhydrous hydrogen bromide gas in a suitable solvent. The resulting linear deblocked hexapeptide may be cyclized to the desired cyclic hexapeptide by any of the carboxyl activating agents known in the art useful for coupling carboxylic acids to amines, for example, an activated ester such as the NHS or NPE or carboxyl activating reagents such as dicyclohexylcarbodiimide, triphenylphosphine/2,2'-pyridyldisulfide (Mukaiyama's reagent); diethylphosphoryl cyanide; isobutyl chloroformate; and Woodward's reagent K. The preferred method in the present invention is the use of diphenylphosphoryl azide.

TABLE I

General Scheme for Preparing Cyclo(Pro-D-Phe)₃

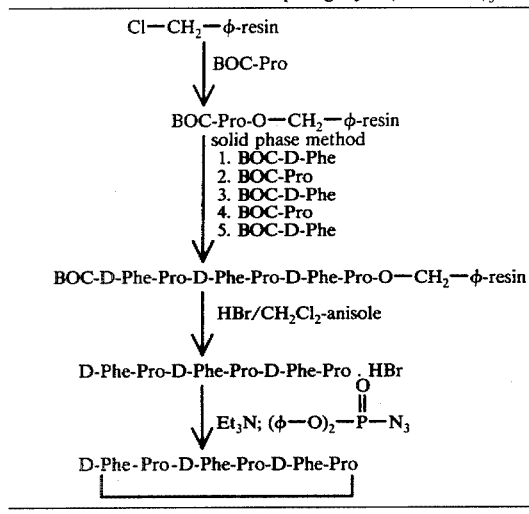

As reference to Table 1 will show, one preferred overall procedure for preparing the desired cyclic hexapeptides of the present invention involves the stepwise synthesis of the linear hexapeptide on a solid phase resin. More specifically, in the process for preparing cyclo(Pro-D-Phe)₃ the carboxyl end of the N-blocked amino acid proline is bound covalently to an insoluble polymeric resin support as the carboxylic acid ester of the resin-bonded benzyl chloride. The amino group of Pro is protected by the BOC group. After the attachment of the Pro is completed on the resin, the protecting group BOC is removed by treatment with HCl in ethyl acetate. The subsequent amino acids are attached, in the form of BOC-amino acid, using DCCI as the condensing agent. After the desired linear hexapeptide has been prepared, it is removed from the resin by treatment with anhydrous hydrogen bromide gas in methylene chlorideanisole (10:1). The resulting linear hexapeptide having the amino acid sequence D-Phe-Pro-D-Phe-Pro-D-Phe-Pro.HBr is treated with diphenylphosphoryl azide in the presence of triethylamine to form the desired cyclic hexapeptide cyclo-(Pro-D-Phe)₃.

To obtain the desired cyclic hexapeptide in pure form any insoluble material in the reaction mixture is removed by filtration and the filtrate evaporated to dryness. The residue containing the crude cyclic hexapeptide is dissolved in a suitable solvent such as 10% aqueous DMF. To this solution is added a mixed-bed ion exchange resin to remove any compounds which have a free amino, acidic hydroxyl, or carboxyl group. The mixed-bed ion exchange resin (with the compounds having free amino, acidic hydroxyl, or carboxyl groups absorbed on it) is removed by filtration and the filtrate is again evaporated to dryness. The residue is redissolved in a suitable solvent such as chloroform. To this solution is slowly added a miscible solvent in which the desired cyclic hexapeptide is insoluble. This results in the crystallization of the cyclic hexapeptide. The final product is then collected by filtration and dried in vacuo.

The following Examples illustrate methods of carrying out the present invention, but it is to be understood that these Examples are given for purposes of illustration and not of limitation.

EXAMPLE 1

Preparation of BOC-(D-Phe-Pro)₃-O-CH₂-φ-resin

Chloromethyl resin, 775.9 g. (2.04 moles), having 2.64 meq. chlorine/g., and 439.4 g. (2.04 moles, 1 equivalent) of BOC-Pro were added to 3713 ml. of peroxide-free tetrahydrofuran. The mixture was stirred in an oil bath at 80° C. bath temperature for 45 minutes. Triethylamine, 267.3 ml., was added and the reaction mixture stirred at 80° C. bath temperature for 94 hours, cooled to 25° C. and transferred to a stirred solid phase reaction column with 2276 ml. of tetrahydrofuran. After removal of the solvent, the resin was washed using the stirred column with:

3 × 1485 ml. of tetrahydrofuran
4 × 4460 ml. of ethanol
1 × 4460 ml. of acetic acid
3 × 4460 ml. of water
3 × 4460 ml. of methanol
3 × 4460 ml. of chloroform.

The BOC-Pro-O-CH₂-φ-resin was dried in vacuo at 25° C. for 16 hours, giving 1071 g. of BOC-Pro-O-CH₂-φ-resin containing 1.14 μmole of proline/mg. of resin.

BOC-Pro-O-CH₂-φ-resin (20 g.; 15.6 mmole) was carried through the procedure in Table II, using 2 deblockings (2 minutes and 15 minutes) with HCl in ethyl acetate, and 1.8 equivalents of BOC-D-Phe and 1.8 equivalents of BOC-Pro in alternating sequence until the desired BOC-hexapeptide-O-CH₂-φ-resin was obtained.

TABLE II

| | EtAc-4N HCl | EtAc (1) MeOH (1) CH₂Cl₂ (1) | NEt₃-CH₂Cl₂ (1:9) (2) | CH₂Cl₂ (4) | BOC AA in CH₂Cl₂ | DCCI in CH₂Cl₂ | DMF (1) MeOH (1) CH₂Cl₂ (1) |
|---|---|---|---|---|---|---|---|
| Volume ml. | 300 | 150 | 150 | 150 | 40 | 13 | 150 |
| Time/min. | 2 and 15 | 2 | 2 and 2 | 2 | 2 | 15 | 2 |

The BOC-hexapeptide-O-CH₂φ-resin was washed with:

3 × 250 ml. of ethanol
3 × 150 ml. of acetic acid
5 × 250 ml. of ethanol
3 × 250 ml. methylene chloride.

After the product was dried in vacuo for several days, it weighed 26.7 grams. By weight gain, it contained 0.581 mmole of peptide per gm. By Spinco amino acid analysis, it contained 0.338–0.42 mmole of peptide per gm. Amino acid analysis after hydrolysis yielded the following results:
Pro 1.53 μmole/mg;
D-Phe 1.58 μmole/mg.

EXAMPLE 2

Preparation of Cyclo(Pro-D-Phe)$_3$

BOC-D-Phe-Pro-D-Phe-Pro-D-Phe-Pro-ϕ-CH$_2$-resin, 75 mmole based on the initial amino acid bound to the resin, was suspended in 1000 ml. of methylene chloride to which was added 100 ml. of anisole. Anhydrous hydrogen bromide gas was bubbled through the suspension at room temperature while stirring for 1 hour. The bulk of the excess hydrogen bromide gas and some methylene chloride was removed under water aspirator vacuum while keeping the flask in a lukewarm water bath for 1 hour. The flask was protected from moisture by the use of a CaCl$_2$ drying tube. To the resulting slurry was added 1000 ml. of low boiling petroleum ether. The resin and solids were collected by filtration and washed with 3 × 1 liter ether and dried in vacuo for 2 hours.

The peptide-resin mixture was extracted with degassed dimethylformamide (DMF) 4 × 1000 ml. The DMF solution was diluted to 5.0 liters with additional degassed DMF. The pH of the solution was adjusted to 6.8 by the addition of 35 ml. of triethylamine. The solution was cooled to −25° C. and 20.6 gm. (75 mmole) of diphenylphosphoryl azide was added. The reaction mixture was allowed to stand at −25° C. for 48 hours at which time the reaction was allowed to warm up to room temperature. The reaction solution was filtered to remove insolubles and the filtrate allowed to evaporate in vacuo.

The residue was washed with 2 × 1 liter of water. To the residue was added 500 ml. chloroform followed by 1000 ml. of methanol-water (9:1). Sufficient mixed-bed resin, AG-501-X(8)D, was added with stirring so that the blue color of the resin persisted for ½ hour. The resin was removed by filtration and washed with 150 ml. of chloroform. The washings and the filtrate were combined and evaporated in vacuo.

After repeated evaporation to dryness with ethanol, the residue was dissolved in 150 ml. chloroform and the cyclic peptide precipitated by the slow addition of 500 ml. ether. The crystalline product was collected by filtration, washed with ether and dried in vacuo. Yield, 32.8 grams.

The mother liquor was concentrated in vacuo. The residue was dissolved in 50 ml. chloroform and a second crop of the cyclic peptide was precipitated by the slow addition of 375 ml. ether. The product was collected by filtration and dried in vacuo to yield 6.24 g. of a second crop.

The peptides,
cyclo(D-Pro-Ala)$_3$, cyclo(D-Pro-Phe)$_3$, cyclo(Pro-D-Phe)$_3$, cyclo(Sar-Ala)$_3$, cyclo(Pro-D-Ala)$_3$, cyclo(Sar-D-Phe) (Pro-D-Phe)$_2$, and cyclo(p-chlorophenylalanyl-D-Pro)$_3$ are prepared in the same manner as set forth above for cyclo(Pro-D-Phe)$_3$.

EXAMPLE 3

Preparation of Cyclo(L-Azetidine-2-carbonyl-D-Phe)$_3$

BOC-(L-Azetidine-2-carbonyl-D-Phe)$_3$-O-CH$_2$-ϕ-resin, (prepared by the process set forth in Example 1) 1.0 mmole based on the initial amino acid bound to the resin, was suspended in 25 ml. of methanol to which was added 2.8 ml. of triethylamine. After stirring 24 hours, the solution was separated from the resin by filtration, and the filtrate was evaporated to dryness; the resulting oil was flushed and evaporated to dryness twice with methanol.

This oil (BOC hexapeptide methyl ester) was dissolved in 15 ml. of dioxane to which was added 15 ml. of water, followed by 2.5N sodium hydroxide such that the pH was established at 12 (determined by moistened narrow range pH paper). After 4 hours tlc confirmed the saponification to be complete, so the reaction mixture was adjusted to pH 6 by addition of 0.3M sulfuric acid and evaporated in vacuo to a volume of 5–10 ml. The product was isolated by further acidification to pH 3, addition of water, and extraction into ethyl acetate 3 times. The ethyl acetate extract was washed twice with 50% saturated sodium chloride and dried over anhydrous magnesium sulfate. Evaporation to dryness gave a gum which was converted to solid by dissolving in the minimal amount of ethyl acetate and precipitating by addition of ether, followed by an equal volume of low boiling petroleum ether. The product (BOC hexapeptide acid) was collected by filtration and washed with low boiling petroleum ether, and dried in vacuo. Yield 0.67 g.

This sample was dissolved in 80 ml. of ethyl acetate, through which was passed anhydrous hydrogen chloride gas for 15 minutes at 0° C., then nitrogen for 60 minutes. About 100 ml. of ether was added to insure complete precipitation, and after further bubbling of nitrogen for 30 minutes, the solid was isolated by filtration, washed twice with ether, and dried in vacuo. Addition of an equal volume of low boiling petroleum ether to the filtrate afforded more solid, which was isolated as above.

Both crops of solid were dissolved in 120 ml. dry, degassed DMF, and the solution was adjusted to pH 7.5 by the addition of triethylamine. After cooling to −25° C., 0.18 ml. of diphenylphosphoryl azide was added; after 41 hours the reaction mixture was allowed to warm to 0° C. and the pH was adjusted to 7.5. The pH was adjusted again at 70 hours (reaction incomplete by tlc), and at 135 hours (reaction complete); about 40 ml. of solvent was evaporated in vacuo, and 20 ml. of water plus 60 ml. of AG501-X(8)D resin were added, followed by stirring 4 hours. The still blue resin was separated from solution by filtration and washed twice with DMF. The combined washings and filtrate were evaporated to dryness, flushed and evaporated with two portions of n-butyl alcohol (a small amount of solid was separated from the second n-butyl alcohol wash by filtration). The residual oil was taken up into the minimal amount of chloroform-ethyl acetate, then 30 ml. of ether was added, followed by 250 ml. of low boiling petroleum ether. The resulting solid was isolated by filtration, washed twice with low boiling petroleum ether, and dried in vacuo. Yield 0.28 g.

The effectiveness of the cyclic hexapeptides of the present invention in modifying the ratio of volatile fatty acids produced in the rumen was first illustrated by means of in vitro tests. The test method used is set forth below.

EXAMPLE 4

In Vitro Rumen Fermentation Test of Cyclo(Pro-D-Phe)$_3$

Rumen fluid which contained methane-producing bacteria and other rumen bacteria was produced in a fermentor which was set up and maintained to simulate the conditions of a rumen.

The test was carried out in a screw-cap tube which was sealed with a butyl rubber stopper. The tube contained an incubation mixture consisting of 100 mg. ground feed, 0.5 ml. buffer-salts solution, 3.5 ml. rumen fluid which had been strained through 4 layers of absorbent gauze and 1 mg. of the compound cyclo(Pro-D-Phe)$_3$. The air in the tube was replaced with a gas mixture of 97% nitrogen-3% hydrogen made free of oxygen by passage through a catalytic purifier. After incubation for 18 hours in a water bath shaker at 39° C., 0.5 ml. of the gas was removed through the stopper into the sample loop of a Fisher Gas Partitioner. The gas sample was partitioned, and the methane produced was compared to a standard gas mixture containing a known amount of methane. The incubation mixture was acidified with 4 ml. of 10% metaphosphoric acid and centrifuged. One $\mu$l. of the supernate was analyzed by gas-liquid chromatography. The volatile fatty acids were compared to a standard volatile fatty acid mixture containing known amounts of acetic, propionic, butyric and valeric acids. Appropriate controls were included. At a level of 250 $\mu$g./ml. of the tested compound, CH$_4$ was essentially eliminated. There was a significant shift in VFA ratios favoring the longer chain acids.

| Control: | $\mu$mols % | $\mu$mols |
|---|---|---|
| Acetic | 58.5 | 39.9 |
| Propionic | 28.5 | 19.5 |
| Butyric | 10.5 | 7.1 |
| Valeric | 3.0 | 1.8 |
| Total | 100.5% | 68.3 |
| Treated 16 $\mu$g./ml. | $\mu$mols % | $\mu$mols |
| Acetic | 31.0 | 18.8 |
| Propionic | 37.0 | 23.0 |
| Butyric | 25.0 | 15.3 |
| Valeric | 7.0 | 4.5 |
| Total | 100.0% | 61.6 |

The data tabulated above shows that the cyclic hexapeptide cyclo(Pro-D-Phe)$_3$ is effective in increasing the production of the VFAs, propionic, butyric and valeric at the expense of methane and acetate.

Administration of the cyclic hexapeptides of the present invention prevents and treats ketosis as well as improves feed utilization.

It has been found that the cyclic hexapeptides of the present invention used in this novel method increase the efficiency of feed utilization in ruminant animals. The easiest way to administer the compounds is by mixing them in the animal's feed.

However, the compounds can be usefully administered in other ways. For example, they can be incorporated into tablets, drenches, salt blocks for pasture use, paste, boluses, or capsules and dosed to the animals.

Formulation of the compounds in such dosage forms can be accomplished by means of methods well known in the veterinary pharmaceutical art. Each individual dosage unit should contain a quantity of the feed-efficiency-improving compound which has a direct relation to the proper daily dose for the animal to be treated.

Capsules are readily produced by filling gelatin capsules with any desired form of the desired compound. If desired, the compound can be diluted with an inert powdered diluent. Tablets of the compounds useful in this novel method are made by conventional pharmaceutical processes. Manufacture of tablets is a well-known and highly-advanced art. In addition to the active ingredient, a tablet usually contains a base, a disintegrator, an absorbent, a binder, and a lubricant.

Drenches of the compounds are prepared most easily by choosing a water-soluble form of the compound. If an insoluble form is desired for some reason, a suspension may be made. Alternatively, a drench may be formulated as a solution in a physiologically-acceptable solvent such as a polyethylene glycol.

Suspensions of insoluble forms of the compound can be prepared in non-solvents such as vegetable oils such as peanut, corn, or sesame oil; in a glycol such as propylene glycol or a polyethylene glycol; or in water, depending on the form of the compound chosen.

These compounds may also be administered in the drinking water of the ruminants. Incorporation into drinking water is performed by adding a water soluble or water-suspendable form of desired compounds in the water in the proper amount. Formulation of the compounds for addition to drinking water follows the same principles as formulation of drenches.

In the field the active ingredients may be administered by means of salt or molasses blocks. A typical block may be prepared using the following ingredients:

| Ingredient | Weight per cent |
|---|---|
| Dried cane molasses | 44.54 |
| Ground soybean hulls | 24.90 |
| Cyclo(Pro-D-Phe)$_3$ | 10.00 |
| Granulated salt | 21.59 |
| Trace minerals and vitamins | 0.20 |
| Stabilized animal fat | 1.11 |
| Moisture | 2.66 |

The most practical way to treat animals with the compounds of this invention is by the formulation of the compounds into the feed supply. Any type of feed may be medicated with the compounds, including common dry feeds, liquid feeds, and pelleted feeds.

The methods of formulating drugs into animal feeds are well known. It is usual to make a concentrated drug premix as a raw material for medicated feeds. For example, typical drug premixes may contain from about 0.1 to 50% by weight of the active compound. Especially preferred are premixes containing 2 to 25% by weight of the active compound. The wide range results from the wide range of concentration of compound which may be desired in the final feed. Premixes may be either liquid or solid.

The formulation of ruminant feeds containing the proper amounts of the compounds for useful treatment is mainly a matter of arithmetic. It is necessary only to calculate the amount of compound which is desired to administer to each animal, to take into account the amount of feed per day which the animal eats, and the concentration of compound in the premix to be used, and calculate the proper amount of premix to be blended into the final feed.

The cyclic peptides of this invention find their primary use in the treatment of ruminants such as sheep and cattle. The optimum amount of the cyclic peptide to be employed for the treatment of a particular animal, will depend on the particular peptide employed, the species of animal to be treated, and the weight of the animal. Generally, good results are obtained with the cyclic peptides of this invention by the oral administration of feed containing from about 0.00005 to about 0.5% of the cyclic hexapeptides the preferred range being about 0.00025 to about 0.1%. With the preferred cyclic hexapeptide of this invention, cyclo(Pro-D-Phe)$_3$, excellent improvement of feed utilization is obtained in cattle and sheep by administering feed containing from about 0.0025 to about 0.01% of the active ingredient.

All of the methods of formulation, mixing, and pelleting feeds which are normally used in the ruminant feed art are entirely appropriate for manufacturing feed containing the compounds usable in this method.

It is not intended that the scope of this invention be limited to any particular formulations or methods of administration. The invention is a method of increasing the efficiency of feed utilization by ruminant animals by the oral administration of certain compounds, regardless of the method of administration of the compounds.

What is claimed is:

1. The peptides having the structure:
cyclo[(N-alkylamino acid)-X-(N-alkylamino acid)'-X-(N-alkylamino acid)"-X]
wherein (N-alkylamino acid), (N-alkylamino acid)' and (N-alkylamino acid)" have the structure:

$$\begin{array}{c} R^1 \; R^2 \; O \\ | \; \; | \; \; \| \\ -N-CH-C- \end{array}$$

wherein $R^1$ is a lower alkyl group having 1 to 3 carbon atoms and $R^2$ is hydrogen and methyl or $R^1$ and $R^2$ are $-(CH_2)_n-$, n being an integer 2 or 3, and form a 4- or 5-membered ring; and X is D- or L-Ala, D- or L-Phe, D- or L-Leu, D- or L-p-halophenylalanyl or D- or L-p-nitrophenylalanyl, with the proviso that when $R^1$ is methyl and $R^2$ is hydrogen, X is not D-Ala.

2. The peptides according to claim 1 wherein (N-alkylamino acid), (N-alkylamino acid)' and (N-alkylamino acid)" are selected from the group consisting of Sar, D- or L-Pro and X is D- or L-Ala or D- or L-Phe and wherein when Pro is D, X is L-Ala or L-Phe or L-p-chlorophenylalanyl or L-p-nitrophenylalanyl; and when Pro is L, X is D-Ala or D-Phe or D-p-chlorophenylalanyl or D-p-nitrophenylalanyl; and wherein when N-alkylamino acid is Sar, X is not D-Ala or D- or L-Phe.

3. The peptides according to claim 2 having the structure:
cyclo(D-Pro-Ala)$_3$, cyclo(D-Pro-Phe)$_3$, cyclo(Pro-D-Phe)$_3$, cyclo(Sar-Ala)$_3$, cyclo(Pro-D-Ala)$_3$, cyclo(Sar-D-Phe) (Pro-D-Phe)$_2$, and cyclo(p-chlorophenylalanyl-D-Pro)$_3$.

4. The peptide according to claim 3 having the structure:

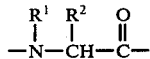

5. The peptide according to claim 3 having the structure:

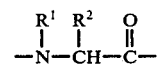

6. The peptide according to claim 3 having the structure:

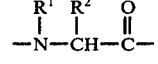

7. A composition useful for increasing the efficiency of feed utilization by ruminant animals having a developed rumen function comprising an inert carrier and a VFA-increasing amount of the peptide having the structure:
cyclo[(N-alkylamino acid)-X-(N-alkylamino acid)'-X-(N-alkylamino acid)"-X]
wherein (N-alkylamino acid), (N-alkylamino acid)' and (N-alkylamino acid)" have the structure:

$$\begin{array}{c} R^1 \; R^2 \; O \\ | \; \; | \; \; \| \\ -N-CH-C- \end{array}$$

wherein $R^1$ is a lower alkyl group having 1 to 3 carbon atoms and $R^2$ is hydrogen and methyl or $R^1$ and $R^2$ are $-(CH_2)_n-$, n being an integer 2 or 3, and form a 4- or 5-membered ring; and X is D- or L-Ala, D- or L-Phe, D- or L-Leu, D- or L-p-halophenylalanyl or D- or L-p-nitrophenylalanyl, with the proviso that when $R^1$ is methyl and $R^2$ is hydrogen, X is not D-Ala.

8. A composition according to claim 7 wherein said compound comprises from about 0.00005 to about 0.5% by weight of said composition.

9. A composition according to claim 7 wherein said compound comprises from about 0.00025 to about 0.1% by weight of said composition.

10. A concentrated premix composition for addition to the feed of a ruminant, useful for the increased utilization of feed, which comprises from about 0.1 to about 50% by weight of the peptide having the structure:
cyclo[(N-alkylamino acid)-X-(N-alkylamino acid)'-X-(N-alkylamino acid)"-X]
wherein (N-alkylamino acid), (N-alkylamino acid)' and (N-alkylamino acid)" have the structure:

$$\begin{array}{c} R^1 \; R^2 \; O \\ | \; \; | \; \; \| \\ -N-CH-C- \end{array}$$

wherein $R^1$ is a lower alkyl group having 1 to 3 carbon atoms and $R^2$ is hydrogen and methyl or $R^1$ and $R^2$ are $-(CH_2)_n-$, n being an integer 2 or 3, and form a 4- or 5-membered ring; and X is D- or L-Ala, D- or L-Phe, D- or L-Leu, D- or L-p-halophenylalanyl or D- or L-p-nitrophenylalanyl, with the proviso that when $R^1$ is methyl and $R^2$ is hydrogen, X is not D-Ala and an inert carrier.

11. The concentrated premix composition of claim 10 which comprises from about 2 to about 25% by weight of said peptide.

* * * * *